United States Patent [19]

Ishida

[11] 4,409,018
[45] Oct. 11, 1983

[54] HEXAHYDROISOINDOL DERIVATIVES, AND THEIR PRODUCTION AND USE

[75] Inventor: Yasuo Ishida, Suita, Japan

[73] Assignee: Takeda Chemical Industries, Ltd., Osaka, Japan

[21] Appl. No.: 267,681

[22] Filed: May 28, 1981

[30] Foreign Application Priority Data

May 30, 1980 [JP] Japan .................. 55-72949

[51] Int. Cl.³ .................. A01N 43/38; C07D 209/46
[52] U.S. Cl. .................. 71/96; 548/461; 548/513
[58] Field of Search .................. 71/96; 260/325 PH; 548/476, 461, 513

[56] References Cited

U.S. PATENT DOCUMENTS

B 536,322  3/1976  Goddard .................. 71/96
4,032,326  6/1977  Goddard .................. 71/96
4,312,809  1/1982  Haugwitz .................. 260/325 PH

FOREIGN PATENT DOCUMENTS 2831770  2/1979  Fed. Rep. of Germany .

OTHER PUBLICATIONS

Chem. Abstract, 88:37608x (1978), Herbicidal N--phenyl-3,4,5,6-tetrahydromonothiophthalimides.

Primary Examiner—Donald G. Daus
Assistant Examiner—M. C. Eakin
Attorney, Agent, or Firm—Burgess, Ryan & Wayne

[57] ABSTRACT

Novel compounds of the formula

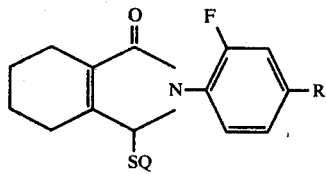

wherein R is a halogen, Q is hydrogen, a substituted or unsubstituted hydrocarbon,

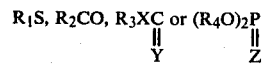

(wherein $R_1$ is a substituted or unsubstituted hydrocarbon or

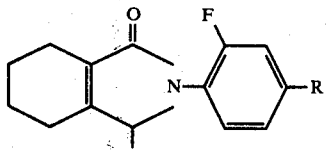

$R_2$ is hydrogen or a substituted or unsubstituted hydrocarbon, $R_3$ is a substituted or unsubstituted hydrocarbon, $R_4$ is a lower alkyl group, X is oxygen or an imino group which may be substituted by a lower alkyl, and each of Y and Z is oxygen or sulfur); which are useful as herbicides.

21 Claims, No Drawings

HEXAHYDROISOINDOL DERIVATIVES, AND THEIR PRODUCTION AND USE

The present invention relates to novel hexahydroisoindole derivatives, to processes for producing the same, and to herbicides containing said derivatives.

More particularly, the present invention relates to:
1. A compound represented by the formula

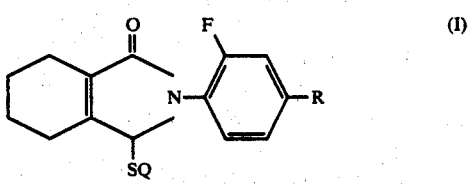

wherein R is a halogen, Q is hydrogen, a substituted or unsubstituted hydrocarbon

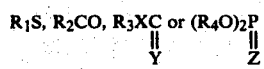

(wherein $R_1$ is a substituted or unsubstituted hydrocarbon or

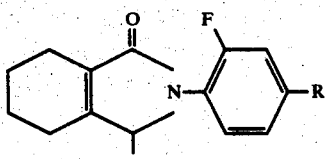

$R_2$ is hydrogen or a substituted or unsubstituted hydrocarbon, $R_3$ is a substituted or unsubstituted hydrocarbon, $R_4$ is a lower alkyl group, X is oxygen or an imino group which may be substituted by a lower alkyl, and each of Y and Z is oxygen or sulfur);
2. Processes for producing the compound (I), and
3. A herbicide having as an active ingredient the compound (I).

A large number of chemical agents have been so far utilized as herbicides, but very few have been satisfactory in terms of herbicidal effect against weeds, phytotoxicity to crops, toxicities to man and animals and fishes and shellfishes, environment pollution, etc. Therefore, strongly demanded is the development of chemical agents that are to be further improved in such respects.

The present inventor, after continued intensive research made with a specific view to resolving such problems, found that the above-mentioned novel compound (I) possesses strong herbicidal activities, and the finding, followed by additional investigation, had led to the completion of the present invention.

Thus, the above-mentioned novel compounds (I) not only possess excellent weed-killing action against a wide range of weeds such as paddy-field weeds, e.g., Barnyardgrass (*Echinochloa oryzicola Vasing*), Tamagayatsuri (*Cyperus difformis L.*), Konagi (*Monochoria vaginalis Presl.*), Azena (*Lindernia procumbens Philcox*), Kikashigusa (*Rotala indica koehne*) and Spike rush (*Eleocharis acicularis Roem.* et Schult.), and field weeds, e.g., crab-grass (*Digitaria adsendens Henr*), Pigweed (*Amaranthus retroflexus L.*), Lamb's quarters (*Chenopodium album L.* Var. *Centrobrum Makino*), Inutade (*Polygonum Blumie Meisn*), common puslane (*Portulaca oleracea L.*) and Green foxtail (*Setaria Viridics Blauv.*) but also exhibit exceedingly high selectivity for some crops such as leguminous plants, e.g., soybean, and cotton, when they are applied by the pre-emergence soil treatment. In addition, the compounds (I) can be safely utilized from the standpoint of toxicity and environment pollution.

In the general formula (I), Q is hydrogen, a substituted or unsubstituted hydrocarbon group or

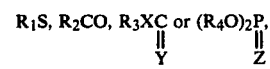

wherein the hydrocarbon group represents straight-chain or branched alkyl groups (preferably, not higher than $C_{11}$) such as methyl, ethyl, propyl, isopropyl, butyl, isobutyl, sec-butyl, tert-butyl, pentyl, isopentyl, neopentyl, hexyl, heptyl, octyl, nonyl, decyl and undecyl, aralkyl groups such as benzyl and phenethye, alkenyl groups (preferably, not higher than $C_6$) such as allyl, methallyl, pentenyl, butenyl and hexenyl, and aryl groups such as phenyl and naphthyl; these hydrocarbon group may be substituted by a halogen such as fluorine, chlorine, bromine and iodine, a lower alkyl group (preferably, $C_1$–$C_4$) such as methyl, ethyl, propyl, isopropyl and butyl, an alkoxy group (preferably, $C_1$–$C_4$) such as methoxy, ethoxy, propoxy and butoxy, hydroxyl group, cyano group, formyl group, carboxyl group, an alkanoyl group (preferably, $C_2$–$C_4$) such as acetyl, propionyl and butyloyl, and aroyl group such as benzoyl, and a lower alkoxycarbonyl group (preferably, $C_1$–$C_4$) such as methoxycarbonyl, ethoxycarbonyl, propoxycarbonyl and butoxycarbonyl.

The hydrocarbon group represented by $R_1$, $R_2$ and $R_3$ also are as defined above. In the case of Q representing

X is oxygen or an imino group which may be substituted by a lower alkyl group as described above, and Y is oxygen or sulfur. In the case of Q designating

$R_4$ is a lower alkyl group as described above, and Z is oxygen or sulfur.

When, in the compound (I) of the present invention, Q is hydrogen, salts with alkali metals such as sodium and potassium, salts with alkaline earth metals such as calcium, salts with organic amines such as triethylamine, and the like fall into the scope of the present invention, as well.

The preferred compounds of the present invention are those of general formula (I) where R is chlorine and Q is hydrogen $R_1S$, $R_2CO$ or

When Q is not hydrogen, preferred compounds are those where $R_1$ is a lower alkyl, phenyl, p-chlorophenyl or

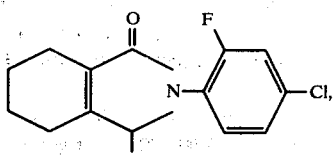

$R_2$ is a straight-chain lower alkyl, $R_3$ is lower alkyl, cyclohexyl, allyl, benzyl, phenyl, p-chlorophenyl or p-tolyl, and Y is oxygen or sulfur.

The novel compound (I') can be produced for example by the reduction of the compound (II). In the reduction reaction, reducing agents such as metal borohydride compounds, e.g., sodium borohydride and lithium borohydride, and mercaptans, e.g., alkyl mercaptans ($C_1$-$C_4$), benzyl mercaptans and thiophenol are utilized. In the case of mercaptans being utilized, they are preferably added in the proportion of 2 to 5 moles for each mole of (II). The reaction is normally conducted in alcohols such as methanol, ethanol and isopropanol, ethers such as diethyl ether, tetrahydrofuran and 1,2-dimethoxydiethane, and inert solvents such as dioxane, dichloromethane, chloroform, carbon tetrachloride and toluene. In the case of mercaptans being utilized, the reaction is favorably carried out by allowing amines such as ammonia, methylamine, ethylamine, propylamine and butylamine to coexist in quantities equimolar with, or slightly excessive over, the compound (II) to thereby separate out the product as an insoluble salt.

Also, the compound (I'), when it is subjected to a substitution or addition reaction on the sulfur atom, gives a hexahydroisoindole derivative represented by the general formula (I''). The said substitution reaction covers the action of a compound of the general formula Q'X (wherein Q' is as defined above; X is a group removable by the substitution reaction, such as a halogen atom) on the compound (I'). Dimerization with the use of a mild oxidizing agent such as iodine, bromine, ferric ions or hydrogen peroxide is included in this substitution reaction as well. As Q'X, use is made of alkyl halides such as methyl iodide, ethyl bromide and propyl chloride, carboxylic acid halides such as benzoyl chloride, halogenated carbonic acid esters such as ethyl chloroformate, carbamoyl chlorides such as N,N-dimethylcarbamoyl chloride, O,O-dialkylphosphoryl chlorides such as O,O-diethylphosphoryl chloride, or O,O-dialkylthiophosphoryl chlorides, acid anhydrides such as acetic anhydride, sulfenyl chloride, mercaptophthalimide derivatives such as N-alkylthio- or N-arylthiophthalimides, alkyl thiol sulfonates, Bunte salt, etc.

The reaction in which Q'X is used is desirably conducted in a suitable solvent such as inert solvents, e.g., hexane, toluene, dichloromethane, chloroform, carbon tetrachloride, diethyl ether, tetrahydrofuran, dioxane, acetonitrile, ethyl acetate, dimethylformamide, acetone, methanol, ethanol and water. In the reaction with the use of an oxidizing agent such as iodine, bromine, hydrogen peroxide and ferric ions, use can be made of organic acids such as acetic acid and propionic acid as the solvent.

The substitution reaction in which Q'X is used is favorably conducted in the presence of organic and inorganic bases such as pyridine, triethylamine, sodium hydrogencarbonate, potassium carbonate and sodium hydroxide. The reaction temperature is 0° to 100° C., particularly desirably 0° to 60° C.

In the addition reaction to the compound (I'), use is made of isocyanates such as methyl isocyanate and phenyl isocyanate, isothiocyanates such as cyclohexyl isothiocyanate and benzyl isothiocyanate, active unsaturated compounds such as acrolein, ethyl acrylate and acrylonitrile, or alkylene oxides such as ethylene oxide.

The reaction is preferably conducted in an aprotic solvent such as toluene, dichloromethane, chloroform, diethyl ether, dioxane and acetonitrile. The said reaction is accelerated by basic catalysts such as pyridine, triethylamine and sodium hydroxide. Normally, the reaction temperature is preferably 0° to 100° C.

The compound (I'') is produced by the reaction of a compound of the general formula Q'SH [wherein Q' is as defined above] or a salt thereof with the compound (III).

As the compound represented by Q'SH or a salt thereof, use is for example made of mercaptans, thiophenols, thiocarboxylic acids, xanthates, dithiocarbamates, etc. This reaction, when Q'SH is used in the free form, is preferably conducted normally in the presence of a base such as pyridine, triethylamine, sodium hydrogencarbonate, potassium carbonate, calcium carbonate and sodium hydroxide. This reaction is favorably conducted in an aprotic solvent such as toluene, dichloromethane, chloroform, carbon tetrachloride, diethyl ether, tetrahydrofuran, dioxane, ethyl acetate, acetone, acetonitrile and dimethylformamide. The reaction temperature is suitably 0° to 100° C.

The compound of the general formula (I) where Q is $R_1S$- can also be produced by the reaction between a compound of the general formula (II) and mercaptans in the presence of a base such as triethylamine. The said reaction is normally conducted with the use of a mercaptan in a slightly excessive amount, preferably two- to five-fold. The reaction is conveniently conducted in an inert solvent such as hexane, toluene, dichloromethane, chloroform, carbon tetrachloride, diethyl ether, tetrahydrofuran, dioxane, ethyl acetate, acetone, acetonitrile, dimethylformamide, methanol and ethanol. The reaction is carried out normally 0° to 100° C., preferably 10° to 40° C.

The compound (I) thus obtained can be isolated and purified by the procedures known per se such as concentration, concentration under reduced pressure, solvent extraction, phase transfer, crystallization, recrystallization and chromatographic separation.

The starting compounds (II) used in the present invention can be produced, for example, by the procedure as shown by the following reaction schema.

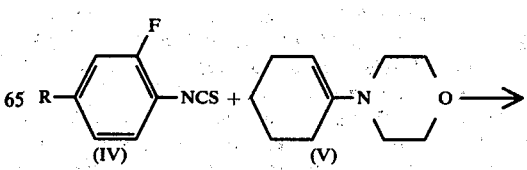

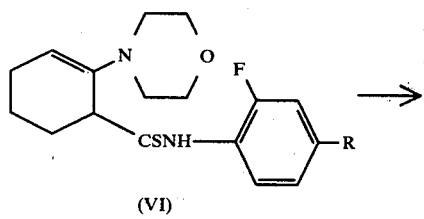

(VI)

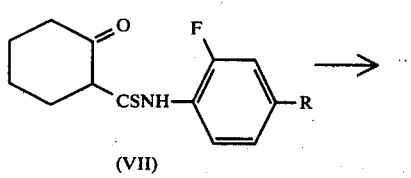

(VII)

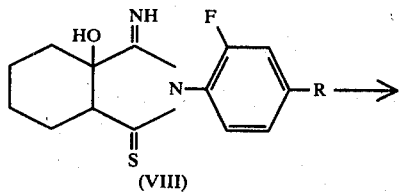

(VIII)

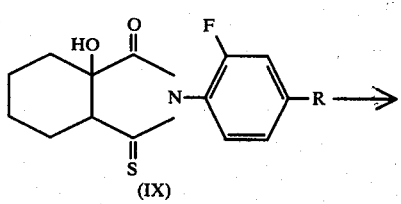

(IX)

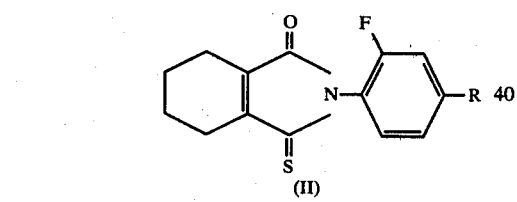

(II)

The compound represented by (VII) in the above-mentioned reaction schema can be produced from the compounds (IV) and (V) via the compound (VI) in accordance with the procedure as described in Chemische Berichte, vol. 95, pp. 926 (1962) and Liebigs Annalen der Chemie, vol. 673, pp. 132 (1964). The compound (VII) thus obtained, when it is reacted with acetone cyanhydrin in the presence of for example potassium carbonate, yields the compound (VIII), which is hydrolyzed after isolation or directly without isolation to form the compound (IX). The compound (IX) undergoes a dehydration reaction with acetic anhydride-pyridine to yield the compound (II). The compound (II) can also be produced from the compound (X) described in U.S. Pat. No. 4,032,326 in accordance with the procedure stated in Japanese Published Unexamined Patent Application No. 83544/1977, as is illustrated in the following reaction schema.

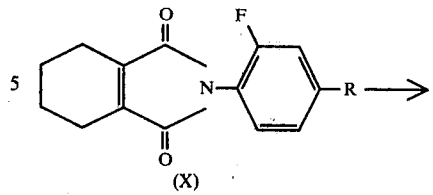

(X)

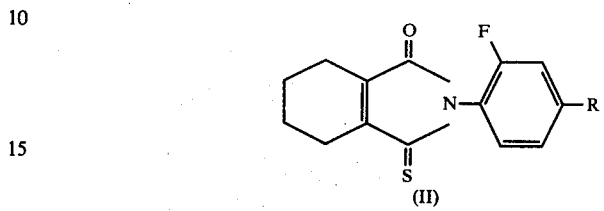

(II)

On the other hand, the starting compound (III) used in the present invention can be produced for example by the procedure as shown in the following reaction schema.

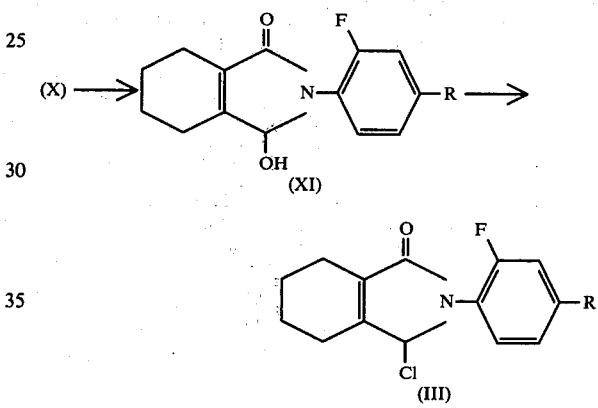

In accordance with the procedure described in Journal of Organic Chemistry, vol. 26, pp. 2273 (1961), reduction is conducted with sodium borohydride to produce the compound (XI), which is reacted with thionyl chloride by the conventional procedure, thereby permitting the production of the compound (III). In addition, the starting compound (II) can also be produced by reacting the compound (III) with for example, sodium benzene thiolsulfonate.

In utilizing the compound (I) of the present invention as herbicides, one or not less than two kinds of the compound (I), depending upon the application purpose, are dissolved, or suspended, in suitable liquid carriers (for example, solvent) or mixed with, or adsorbed on, appropriate solid carriers (for example, diluent and dust carrier), followed by adding emulsifiers, suspending agents, spreaders, penetrants, wetting agents, thickening agents, stabilizers, etc., if necessary, to thereby apply in the preparation forms such as oil solution, emulsifiable concentrates, wettable powders, dusts, granules, tablets, sprays and ointments. Such preparations can be prepared by the procedures known per se.

The proportion in which the active ingredient is contained in the herbicides varies with the intended application purpose but is suitably in the range of 10 to 90 weight % for emulsifiable concentrates, wettable powders, etc., appropriately in the region of 0.1 to 10 weight % for oil solution, dusts, etc., and properly in the range of 1 to 20 weight % for granules, although such concentrations may be conveniently changed with the intended application purpose.

Emulsifiable concentrates, wettable powders, etc. may better be sprayed after diluting and extending suitably with water, etc. (for example, 100 to 100,000 times) on the occasion of application.

Suitable examples of the liquid carrier (solvent) which are used in the herbicides includes solvents such as water, alcohols (e.g., methyl alcohol, ethyl alcohol, ethylene glycol, etc.), ketones (e.g., acetone, methyl ethyl ketone, etc.), ethers (e.g., dioxane, tetrahydrofuran, cellosolve, etc.), aliphatic hydrocarbons (e.g., gasoline, kerosene, light oil, fuel oil, machine oil, etc.), aromatic hydrocarbons (e.g., benzene, toluene, xylene, solvent naphtha, methylnaphthalene, etc.) and halogenated hydrocarbons (e.g., chloroform, carbon tetrachloride, etc.), acid amides (e.g., dimethylformamide), esters (e.g., ethyl acetate, butyl acetate, glycerine esters of fatty acids, etc.) and nitriles (e.g., acetonitrile), and mixtures of one or not less than two kinds of these are utilized. As the solid carrier (diluent, dust-diluent), use is made of vegetable powders (e.g., soybean meal, tobacco meal, wheat flour, wood flour, etc.), mineral powders (e.g., clay such as kaolin, bentonite and acid clay, talc such as talc powder and pencile stone powder, silicas such as diatomaceous earth and mica powder, etc.), alumina, sulfur powder, activated carbon and the like, and mixtures of one or not less than two kinds of these are utilized.

As the ointment base, suitably selected can be one or not less than two kinds of polyethylene glycol, pectin, polyhydric alcohol esters of higher fatty acids such as glycerin monostearate, cellulose derivatives such as methyl cellulose, sodium arginate, bentonite, higher alcohols, polyhydric alcohols such as glycerine, petrolatum, white petrolatum, liquid paraffin, lard, various kinds of vegetable oils, lanolin, lanolin anhydricum, hardened oil, waxes, resins, etc., either solely or added with various surfactants and others.

As the surfactants which are used as emulsifiers, spreaders, penetrants, dispersing agents, etc., use is made of soaps, polyoxyalkyl aryl esters (e.g., Nonal ®) produced by Takemoto Oils & Fats Co. Japan), alkyl sulfates (e.g., Emal 10 ®, Emal 40 ® etc. produced by Kao Atlas Co. Japan), alkyl sulfonates (e.g., Neogen ®, Eeogen T ®, etc. produced by Dai-ichi Seiyaku Kogyo Co. Japan: Neoplex ® produced by Kao Atlas Co. Japan), polyethylene glycol ethers (e.g., Nonipol 85 ®, Nonipol 100 ®, Nonipol 160 ®, etc. produced by Sanyo Chemical Industries, Japan), polyhydric alcohol esters (e.g., Tween 20 ®, Tween 80 ®, etc. produced by Kao Atlas Co. Japan), etc. if necessary.

In utilizing the compounds (I) as herbicides, their application amount is about 1 to 50 g, perferably about 2 to 40 g, per are of a paddy field, and about 1 to 50 g, preferably about 2 to 40 g, per are of a blowed field. In addition, it is suitable to use the compounds (I) as a pre-emergence treatment agent. The compounds (I) show lowered toxicity to for example mammals and fishes, and can be safely used as pesticides.

Also, the compounds (I) can be used as mixtures by formulating a herbicide containing the compound (I) with other kinds of herbicides, plant growth regulators, fungicides (e.g., organic chlorine-based fungicides, organic sulfur-based fungicides, antibiotics, etc.), insecticides (e.g., organic phosphorus based insecticides, naturally occurring insecticides, etc.), mitecides, nematocides, synergists, attractants, repellents, coloring matters, fertilizers, etc. Described in the following are the reference examples, examples and test examples to illustrate the content of this invention in detail.

REFERENCE EXAMPLE 1

4'-Chloro-2'-fluoro-2-morpholino-2-cyclohexene-1-thiocarboxanilide

In 400 ml of chloroform was dissolved 78.9 g of 4-chloro-2-fluorophenyl isothiocyanate, and 68.6 g of 1-morpholino-1-cyclohexene was added dropwise to the solution with stirring over a 10-minute period. After stirring was continued at room temperature for 10 hours, the reaction mixture was concentrated under reduced pressure, and the residue was treated with a small amount of cold ethanol. The resulting crystals were collected by filtration, and there was obtained 127.9 g (yield of 86%) of the subject compound, m.p. 86°–88° C.

REFERENCE EXAMPLE 2

4'-Chloro-2'-fluoro-2-oxo-cyclohexane-1-thiocarboxanilide

In 800 ml of dichloromethane was dissolved 88.9 g of 4'-chloro-2'-fluoro-2-morpholino-2-cyclohexene-1-thiocarboxanilide, and the solution was washed twice with dilute hydrochloric acid and once with water and dried over anhydrous sodium sulfate. The dichloromethane was distilled off under reduced pressure, thereby affording 61.7 g (yield of 81%) of crystals of the subject compound. Recrystallization from hexane yielded slightly yellow crystals, m.p. 97°–98° C.

REFERENCE EXAMPLE 3

2-(4-Chloro-2-fluorophenyl)-3a-hydroxy-1-thioxo-octahydroisoindol-3-one

In 500 ml of ethanol were dissolved 59.6 g of 4'-chloro-2'-fluoro-2-oxo-cyclohexene-1-thiocarboxanilide and 28.4 g of acetone cyanhydrin, and 60 ml of 10% aqueous potassium carbonate solution was added to the solution, followed by stirring at room temperature for 5 hours. Upon acidification with dilute hydrochloric acid, there resulted crystals, which were collected by filtration, washed with dilute ethanol and dried, thereby affording 41.3 g (yield of 63%) of the subject compound. Recrystallization from ethanol yielded slightly yellow crystals, m.p. 156°–157° C.

REFERENCE EXAMPLE 4

2-(4-Chloro-2-fluorophenyl)-2,3,4,5,6,7-hexahydro-3-thioxo-1H-isoindol-1-one

In 75 ml of pyridine was dissolved 28.2 g of 2-(4-chloro-2-fluorophenyl)-3a-hydroxy-1-thioxo-octahydroisoindole-3-one, and 30 ml of acetic acid anhydride was added to the solution, which was allowed to stand at room temperature overnight. The reaction mixture was concentrated under reduced pressure, and the residue was dissolved in dichloromethane, washed with water and dried over anhydrous sodium sulfate. After distilling off the dichloromethane, the resulting crystals were washed with a small amount of cold ethanol and dried, thereby affording 25.2 g (yield of 95%) of the subject compound. Recrystallization from ethanol yielded red-purple crystals, m.p. 101°–102° C.

REFERENCE EXAMPLE 5

2-(4-Chloro-2-fluorophenyl)-3-hydroxy-2,3,4,5,6,7-hexahydro-1H-isoindol-1-one In 400 ml of ethanol was dissolved 40.0 g of 2-(4-chloro-2-fluorophenyl)-2,3,4,5,6,7-hexahydro-1H-isoindol-1,3-dione, and 2.4 g of sodium borohydride was added to the solution with stirring over a 30-minute period, while cooling was effected suitably to maintain the reaction temperature at 20° to 30° C. After stirring was continued at room temperature for one hour, the reaction mixture was neutralized with dilute acetic acid and concentrated to about one third of the original volume. Upon cooling, there resulted crystals, which were collected by filtration, washed with water and dried, thereby affording 36.2 g (yield of 90%) of the subject compound. Recrystallization from ethyl acetate yielded white crystals, m.p. 178°–179° C.

REFERENCE EXAMPLE 6

3-Chloro-2-(4-chloro-2-fluorophenyl)-2,3,4,5,6,7-hexahydro-1H-isoindol-1-one In 30 ml of dichloromethane was suspended 21.0 g of 2-(4-chloro-2-fluorophenyl)-3-hydroxy-2,3,4,5,6,7-hexahydro-1H-isoindol-1-one, and 7.5 ml of thionyl chloride was added to the suspension under stirring over a 20-minute period. The reaction mixture was warmed, stirred at 40° to 45° C. for 1 hour and concentrated to dryness under reduced pressure. The residue was dissolved in methylene chloride and, upon addition of hexane, there was produced insoluble matter, which was filtered out. The filtrate was concentrated to dryness under reduced pressure, thereby affording 19.5 g (yield of 87%) of crystals of the subject compound. Recrystallization from cyclohexane yielded white crystals, m.p. 89°–90° C.

EXAMPLE 1

2-[(4-Chloro-2-fluorophenyl)-2,3,4,5,6,7-hexahydro-3-mercapto-1H-isoindo]-1-one

(Method a)

In 270 ml of ethanol was suspended 27.8 g of 2-(4-chloro-2-fluorophenyl)-2,3,4,5,6,7-hexahydro-3-thioxo-1H-isoindol-1-one, and 9.4 g of sodium borohydride was added to the suspension with stirring at room temperature over a 20-minute period. After stirring was continued for 30 minutes, the reaction mixture was acidified (to pH 3 to 4) with dilute hydrochloric acid and concentrated under reduced pressure. The residue was treated with water, and the resulting crystals were collected by filtration, washed with a small amount of cold ethanol and dried, thereby affording 23.7 g (yield of 85%) of the subject compound. Recrystallization from ethanol yielded white crystals, m.p. 85°–86° C.

Method (b)

In 60 ml of ether was dissolved 5.7 g of 2-(4-chloro-2-fluorophenyl)-2,3,4,5,6,7-hexahydro-3-thioxo-1H-isoindol-1-one, and 5.0 g of ethyl mercaptan and 4.4 g of butylamine were added to the solution, followed by stirring at room temperature for 2 hours. The resulting crystals were collected by filtration, washed with ether and dried, thereby affording 4.8 g (yield of 64%) of a butylamine salt of the subject compound. Upon acidification with dilute hydrochloric acid, there resulted the subject compound.

EXAMPLE 2

2-(4-Bromo-2-fluorophenyl)-2,3,4,5,6,7,-hexahydro-3-mercapto-1H-isoindol-1-one By the same procedure as described in Method (a) of Example 1, 55.0 g of 2-(4-bromo-2-fluorophenyl)-2,3,4,5,6,7-hexahydro-3-thioxo-1H-isoindol-1-one was reduced with 18.0 g of sodium borohydride, thereby affording 44.9 g (yield of 81%) of the subject compound. Recrystallization from ethanol yielded white crystals, m.p. 87°–88° C.

EXAMPLE 3

2-(4-Chloro-2-fluorophenyl)-2,3,4,5,6,7-hexahydro-3-methylthio-1H-isoindol-1-one In 10 ml of acetone was dissolved 1.5 g of 2-(4-chloro-2-fluorophenyl)-2,3,4,5,6,7-hexahydro-3-mercapto-1H-isoindol-1-one, and 1.5 g of methyl iodide and 1.3 g of potassium carbonate were added to the solution, followed by stirring at 40° to 50° C. for 5 hours. After cooling, the insoluble matter was filtered out, and the filtrate was concentrated under reduced pressure. The residual, oily substance was purified by means of column chromatography with the use of silica gel (developing solvent of acetone-hexane), thereby producing 1.4 g (yield of 90%) of the subject compound in white crystals, m.p. 97°–98° C.

EXAMPLE 4

2-(4-Chloro-2-fluorophenyl)-2,3,4,5,6,7-hexahydro-3-phenylthio-1H-isoindol-1-one In 30 ml of dichloromethane were dissolved 3.0 g of 3-chloro-2-(4-chloro-2-fluorophenyl)-2,3,4,5,6,7-hexahydro-1H-isoindol-1-one and 1.1 g of thiophenol, and 1.0 g of triethylamine was added to the solution over a 10-minute period, followed by stirring at room temperature for 2 hours. The reaction mixture was washed with water, dried over anhydrous sodium sulfate and freed of the dichloromethane under reduced pressure. The residue was purified by means of column chromatography with the use of silica gel (developing solvent of dichloromethaneacetone), thereby producing 3.2 g (yield of 86%) of the subject compound in white crystals, m.p. 86°–87° C.

EXAMPLE 5

3-Acetonylthio-2-(4-chloro-2-fluorophenyl)-2,3,4,5,6,7-hexahydro-1H-isoindol-1-one In 10 ml pyridine was dissolved 1.5 g of 2-(4-chloro-2-fluorophenyl)-2,3,4,5,6,7-hexahydro-3-mercapto-1H-isoindol-1-one, and 0.6 g of chloroacetone was added dropwise to the mixture with stirring with cooling at 5° to 10° C. over a period of 10 minutes. After cooling was continued at room temperature for 2 hours, water was added to the mixture for extraction with dichloromethane. The dichloromethane layer was separated out, washed with dilute hydrochloric acid and water, successively, and dried over anhydrous sodium sulfate. The dichloromethane was distilled off under reduced pressure, and the resulting crystals were washed with a mixed solvent of ether and hexane and dried, thereby producing 1.3 g (yield of 73%) of the subject compound. Recrystallization from ethanol yielded white crystals, m.p. 131°–132° C.

EXAMPLE 6

2-(4-Chloro-2-fluorophenyl)-3-(2-cyanoethylthio)-2,3,4,5,6,7-hexahydro-1H-isoindol-1-one In 15 ml of dioxane was dissolved 2.1 g of 2-(4-chloro-2-fluorophenyl)-2,3,4,5,6,7-hexahydro-3-mercapto-1H-isoindole-1-on, and 1.5 g of acrylonitrile, together with several drops of triethylamine, was added, followed by heating at 85° to 90° C. for 6 hours. The reaction solution was concentrated under reduced pressure, and the residual, oily substance was purified by means of column chromatography with the use of silica gel (acetone:hexane=1:3), thereby producing 1.5 g of the subject compound in white crystals, m.p. 101°–103° C.

EXAMPLE 7

2-(4-Chloro-2-fluorophenyl)-2,3,4,5,6,7-hexahydro-3-phenyldithio-1H-isoindol-1-one In 30 ml of toluene were dissolved 3.0 g of 2-(4-chloro-2-fluorophenyl)-2,3,4,5,6,7-hexahydro-3-mercapto-1H-isoindol 1-one and 2.8 g of N-phenylthiophthalimide, and the solution was heated under reflux for 3 hours. Upon cooling, there resulted crystals (phthalimide), which were filtered out, and the filtrate was concentrated under reduced pressure. A small amount of toluene was added and, upon standing overnight, there resulted crystals, which were collected by filtration and dried, thereby producing 2.7 g (yield of 67%) of the subject compound. Recrystallization from toluene yielded white crystals m.p. 127°–129° C.

EXAMPLE 8

2-(4-Bromo-2-fluorophenyl)-3-ethyldithio-2,3,4,5,6,7-hexahydro-1H-isoindol-1-one In 30 ml of ether was dissolved 3.4 g of 2-(4-bromo-2-fluorophenyl)-2,3,4,5,6,7-hexahydro-3-thioxo-1H-isoindol-1-one, and 3 ml of ethyl mercaptan and 3 ml of triethylamine were added to the solution, followed by stirring at room temperature for 5 hours. The reaction mixture was concentrated under reduced pressure, and the residue was purified by means of column chromatography with the use of silica gel (developing solvent of dichloromethane), thereby producing 2.0 g (yield of 50%) of the subject compound in white crystals, m.p. 83°–84° C.

EXAMPLE 9

Bis-[2-(4-chloro-2-fluorophenyl)-3-oxo-2,3,4,5,6,7-hexahydro-1H-isoindol-1-yl]disulfide In 20 ml of ethanol was dissolved 3.0 g of 2-(4-chloro-2-fluorophenyl)-2,3,4,5,6,7-hexahydro-3-mercapto-1H-isoindol-1-one and 1.4 g of iodine was added to the solution, followed by stirring at room temperature for 5 hours. Upon cooling, there resulted crystals, which were recovered by filtration, washed with ethanol and dried, thereby producing 1.7 g (yield of 57%) of the subject compound. Recrystallization from acetone yielded white crystals, m.p. 146°–147° C.

EXAMPLE 10

3-Acetylthio-2-(4-bromo-2-fluorophenyl)-2,3,4,5,6,7-hexahydro-1H-isoindol-1-one

In 20 ml of pyridine was dissolved 3.4 g of 2-(4-bromo-2-fluorophenyl)-2,3,4,5,5,7-hexahydro-3-mercapto-1H-isoindol 1-one, and 3.0 g of acetic anhydride was added to the solution, followed by stirring at room temperature for 3 hours. The reaction mixture was concentrated under reduced pressure, and the residue was treated with water, followed by extracting with dichloromethane, washing with water and drying over anhydrous sodium sulfate. The dichloroethane was distilled off under reduced pressure, and the resulting crystals were washed with hexane and dried, thereby producing 3.4 g (yield of 90%) of the subject compound. Recrystallization from ethanol yielded white crystals, m.p. 117°–118° C.

EXAMPLE 11

2-(4-Chloro-2-fluorophenyl)-2,3,4,5,6,7-hexahydro-3-methoxycarbonylthio-1H-isoindol-1-one In 20 ml of pyridine was dissolved 3.0 g of 2-(4-chloro-2-fluorophenyl)-2,3,4,5,6,7-hexahydro-3-mercapto-1H-isoindol-1-one, and 1.5 g of methyl chloroformate was added to the solution with stirring with cooling at 5° to 10° C. over a period of 20 minutes. After stirring was effected at the same temperature for 2 hours and then at room temperature for 1 hour, the reaction solution was treated with water, and extracted with dichloromethane, followed by washing with dilute hydrochloric acid and water, successively, and drying over anhydrous sodium sulfate. The dichloromethane was distilled off under reduced pressure, and the residual, oily substance was purified by means of column chromatography with the use of silica gel (developing solvent of acetone-hexane), thereby producing 3.0 g (yield of 84%) of the subject compound in white crystals, m.p. 80°–81° C.

EXAMPLE 12

2-(4-Chloro-2-fluorophenyl)-3-(N-phenylcarbamoylthio)-2,3,4,5,6,7-hexahydro-1H-isoindol-1-one In 20 ml of dichloromethane was dissolved 3.0 g of 2-(4-chloro-2-fluorophenyl)-2,3,4,5,6,7-hexahydro-3-mercapto-1H-isoindol-1-one, and 1.3 g of phenyl isocyanate, together with one drop of triethylamine, was added to the solution, followed by stirring at room temperature for 3 hours. The dichloromethane was distilled off under reduced pressure, and the residue was purified by means of column chromatography with the use of silica gel (developing solvent of acetonehexane), thereby producing 3.0 g (yield of 72%) of the subject compound in white crystals, m.p. 135°–136° C.

EXAMPLE 13

2-(4-Bromo-2-fluorophenyl)-3-(N-ethylthiocarbamoylthio)-2,3,4,5,6,7-hexahydro-1H-isoindol-1-one In 20 ml of dichloromethane was dissolved 3.4 g of 2-(4-bromo-2-fluorophenyl)-2,3,4,5,6,7-hexahydro-3-mercapto-1H-isoindol-1-one, and 1.0 g of ethyl isothiocyanate, together with one drop of triethylamine, was added to the solution, followed by stirring at room temperature for 5 hours. The dichloromethane was distilled off under reduced pressure, and the resulting crystals were washed with cold ethanol and dried, thereby producing 3.8 g (yield of 88%) of the subject compound. Recrystallization from ethanol yielded white crystals, m.p. 130°–131° C.

EXAMPLE 14

2-(4-Chloro-2-fluorophenyl)-2,3,4,5,6,7-hexahydro-3-(N-methylthiocarbamoylthio)-1H-isoindol-1-one In 20 ml of dichloromethane was dissolved 3.0 g of 2-(4-chloro-2-fluorophenyl)-2,3,4,5,6,7-hexahydro-3-mercapto-1H-isoindol-1-one, and 0.8 g of methyl isothiocyanate, together with one drop of triethylamine, was added to the solution, followed by stirring at room temperature for 5 hours. The dichloromethane was distilled off under reduced pressure, and the resulting crystals were washed with cold ethanol and dried, thereby producing 3.5 g (yield of 94%) of the subject compound. Recrystallization from ethanol yielded white crystals, 112°–114° C.

EXAMPLE 15

2-(4-Chloro-2-fluorophenyl)-3-(O,O-diethylthionophosphorylthio)-2,3,4,5,6,7-hexahydro-1H-isoindol-1-one In 20 ml of acetone was dissolved 2.0 g of 3-chloro-2-(4-chloro-2-fluorophenyl)-2,3,4,5,6,7-hexahydro-1H-isoindol-1-one, and 1.4 g of sodium O,O-diethyldithiophosphate was added to the solution, followed by stirring at room temperature for 1 hour. After crystals were filtered out, the filtrate was concentrated to dryness under reduced pressure. The residue was treated with cyclohexane, and the insoluble matter was filtered out, and the filtrate was concentrated to dryness under reduced pressure. The resulting crystals were washed with cold hexane and dried, thereby affording 2.3 g (yield of 77%) of white crystals of the subject compound. m.p. 97°–98° C.

Shown in the following table are examples of the compounds obtained by the same procedures as described in the above Examples 1 to 15.

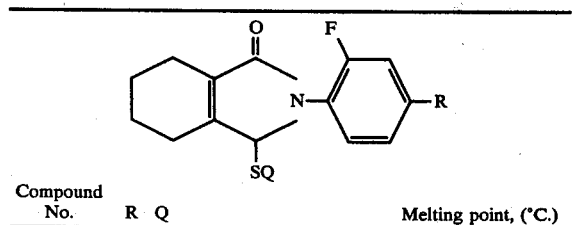

| Compound No. | R | Q | Melting point, (°C.) |
|---|---|---|---|
| 1 | Cl | H | 85–86 |
| 2 | Cl | CH3 | 97–98 |
| 3 | Cl | C2H5 | 63—63 |
| 4 | Cl | C3H7(n) | syrup |
| 5 | Cl | CH2CH=CH2 | syrup |
| 6 | Cl | C4H9(n) | syrup |
| 7 | Cl | C5H11(n) | syrup |
| 8 | Cl | C6H13(n) | syrup |
| 9 | Cl | C6H5 | 86–87 |
| 10 | Cl | CH2C6H5 | 106–107 |
| 11 | Cl | CH2CH2OH | 132–133 |
| 12 | Cl | CH2COCH3 | 131–132 |
| 13 | Cl | CH2CO2C2H5 | syrup |
| 14 | Cl | CH2CH2CO2C2H5 | syrup |
| 15 | Cl | CH2CH2CN | 100–102 |
| 16 | Cl | CH2COC6H5 | 90–91 |
| 17 | Br | H | 87–88 |
| 18 | Br | CH3 | 107–108 |
| 19 | Br | C2H5 | syrup |
| 20 | Br | CH2COCH3 | 104–105 |
| 21 | Br | CH2CH2CN | 130–131 |
| 22 | Cl | SCH3 | 87–88 |
| 23 | Cl | SC2H5 | 79–80 |
| 24 | Cl | SC3H7(n) | 62–63 |
| 25 | Cl | SC4H9(n) | 58–60 |
| 26 | Cl | SC6H5 | 127–129 |

-continued

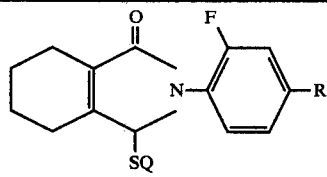

| Compound No. | R | Q | Melting point, (°C.) |
|---|---|---|---|
| 27 | Cl | S—C6H4—Cl | 122–124 |
| 28 | Cl | (isoindolinone-S—) | 146–147 |
| 29 | Br | SCH3 | 115–116 |
| 30 | Br | SC2H5 | 83–84 |
| 31 | Br | SC3H7(n) | syrup |
| 32 | Br | (isoindolinone-S—) | 128–129 |
| 33 | Cl | COCH3 | 108–109 |
| 34 | Cl | COC2H5 | 87–88 |
| 35 | Cl | COC3H7(n) | 62–63 |
| 36 | Cl | COC3H7(i) | syrup |
| 37 | Cl | COC4H9(n) | syrup |
| 38 | Cl | COC4H9(t) | 91–92 |
| 39 | Cl | COC5H11(n) | syrup |
| 40 | Cl | COC6H5 | 53–55 |
| 41 | Cl | CO—C6H4—CH3 | 100–101 |
| 42 | Cl | CO—C6H3Cl2 | 125–126 |
| 43 | Cl | COCH2OCH3 | 105–106 |
| 44 | Br | COCH3 | 117–118 |
| 45 | Br | COC2H5 | 85–86 |
| 46 | Br | COC3H7(n) | 61–62 |
| 47 | Cl | CO2CH3 | 80–81 |
| 48 | Cl | CO2C2H5 | syrup |
| 49 | Cl | CO2C3H7(n) | syrup |
| 50 | Cl | CO2C4H9(n) | syrup |
| 51 | Cl | CO2C5H11(n) | syrup |
| 52 | Cl | CONHCH3 | 169–171 |
| 53 | Cl | CONHC2H5 | 134–135 |
| 54 | Cl | CONHC3H7(n) | 56–58 |
| 55 | Cl | CONHC3H7(i) | 147–148 |
| 56 | Cl | CONHC6H5 | 135–137 |
| 57 | Cl | CONH—C6H4—Cl | 161–163 |
| 58 | Cl | CONH—C6H4—Cl | 160–162 |
| 59 | Cl | CONH—C6H4—CH3 | 163–164 |

-continued

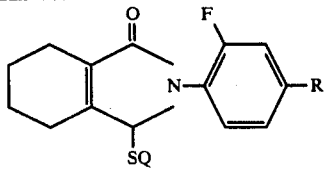

| Compound No. | R | Q | Melting point, (°C.) |
|---|---|---|---|
| 60 | Cl | CSNHCH₃ | 112-114 |
| 61 | Cl | CSNHC₂H₅ | 125-126 |
| 62 | Cl | CSNHCH₂CH=CH₂ | 100-101 |
| 63 | Cl | CSNHC₄H₉(i) | 90-91 |
| 64 | Cl | CSNH—(H) | 131-132 |
| 65 | Cl | CSNHC₆H₅ | 124-125 |
| 66 | Cl | CSNHCH₂C₆H₅ | 139-140 |
| 67 | Cl | CSN(C₂H₅)₂ | 116-117 |
| 68 | Cl | C(S)OC₂H₅ | syrup |
| 69 | Cl | P(S)(OC₂H₅)₂ | 97-98 |
| 70 | Br | CO₂CH₃ | 106-107 |
| 71 | Br | CONHCH₃ | 130-181 |
| 72 | Br | CONHC₂H₅ | 150-151 |
| 73 | Br | CONHC₃H₇(n) | 118-119 |
| 74 | Br | CONHC₄H₉(n) | 119-120 |
| 75 | Br | CONHC₆H₅ | 158-159 |
| 76 | Br | CSNHCH₃ | 126-127 |
| 77 | Br | CSNHC₂H₅ | 130-131 |
| 78 | Br | CSNHCH₂CH=CH₂ | 112-113 |
| 79 | Br | CSNHC₄H₉(i) | 99-100 |
| 80 | Br | CSNH—(H) | 145-146 |
| 81 | Br | CSNH—(phenyl) | 123-125 |
| 82 | Br | CSNH—(phenyl)—Cl | 156-157 |
| 83 | Br | CSNHCH₂—(phenyl) | 145-146 |

EXAMPLE 16

A wettable powder was produced by mixing and pulverizing 30 parts of 2-(4-chloro-2-fluorophenyl)-2,3,4,5,6,7-hexahydro-3-mercapto-1H-isoindol-1-one, 5 parts of sodium ligninsulfonate, 5 parts of polyethylene glycol ether (Nonipol 85 ® produced by Sanyo Chemical Industries, Japan) and 60 parts of clay.

EXAMPLE 17

A granule was produced by adding water to a mixture consisting of 10 parts of 2-(4-chloro-2-fluorophenyl)-2,3,4,5,6,7-hexahydro-3-(N-methylcarbamoylthio)-1H-isoindol-1-one, 5 parts of sodium ligninsulfonate and 85 parts of bentonite, followed by kneading and granulating.

EXAMPLE 18

An emulsifiable concentrate was produced containing 20 parts of 2-(4-chloro-2-fluorophenyl)-2,3,4,5,6,7-hexahydro-3-(N-methylthiocarbamoylthio)-1H-isoindol-1-one, 75 parts of xylene and 5 parts of polyethylene glycol ether (Nonipol 85 ® produced by Sanyo Chemical Industries, Japan).

TEST EXAMPLE 1

Pots of each having 900 cm² made of plastics were respectively filled with filled soil and sown with seeds of crabgrass (*Digitaria adsendens Henr*), Pigweed (*Amaranthus retroflexus L.*), Lamb's-quarters (*Chenopodium album L.* Var. *centrobrum Makino*), Inutade (*Polygonum Blumei Meisn*), common purslane (*Portulaca oleracea L.*), Green foxtail (*Setaria viridis Beauv.*), corn, soybean and cotton, followed by covering 0.5 cm thick with soil. An emulsifiable concentrate containing the compound of the formula (I) was diluted with water to 10 l to make the application rate of the active ingredient [the compound (I)] 5, 10 and 20 g per are, respectively, and sprayed evenly over the soil surfaces by use of a spray gun. 3 weeks later, investigation was carried out for the effect and phytotoxicity of each of the compounds used. 2-(4-chlorophenyl)-2,3,4,5,6,7-hexahydro-3-methylthio-1H-isoindol-1-one, [compound A] was used as a control. The herbicidal effect is indicated by the following indices.

| Index | Effect | Inhibitory rate (%) (weed-killing rate) |
|---|---|---|
| 0 | None | 0 |
| 1 | Negligible | 0.1 to 50 |
| 2 | Poor | 50.1 to 70 |
| 3 | Medium | 70.1 to 87.5 |
| 4 | high | 87.6 to 99.9 |
| 5 | complete | 100 |

Phytotoxicity to crops is indicated by the following indices.

| Index | Phytotoxicity | Percentage of damage (%) |
|---|---|---|
| 0 | None | 0 |
| 1 | Negligible | 0.1 to 12.5 |
| 2 | Slight | 12.6 to 30 |
| 3 | Medium | 30.1 to 50 |
| 4 | Serious | 50.1 to 99.9 |
| 5 | Maximal | 100 |

(It is added that the indices of phytotoxicity to crops, 0 and 1, denote the practical applicability to crops). The results are shown in the following table.

| | Application rate g/a | 1 | | | 2 | | | 3 | | | 4 | | | 5 | | | 6 | | | 7 | | | 8 | | |
|---|---|---|---|---|---|---|---|---|---|---|---|---|---|---|---|---|---|---|---|---|---|---|---|---|---|
| | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 5 | 5 | 5 | 2 | 4 | 5 | 3 | 5 | 5 | 4 | 5 | 5 | 4 | 5 | 5 | 4 | 5 | 5 | 2 | 5 | 5 | 4 | 4 | 5 |
| | Pigweed | 5 | 5 | 5 | 5 | 5 | 5 | 5 | 5 | 5 | 5 | 5 | 4 | 5 | 5 | 1 | 3 | 5 | 5 | 5 | 5 | 5 | 5 | 5 | 5 |
| | Lamb's-quarters | 5 | 5 | 5 | 4 | 5 | 5 | 4 | 5 | 5 | 5 | 5 | 5 | 4 | 5 | 5 | 3 | 4 | 5 | 4 | 5 | 5 | 4 | 5 | 5 |
| | Inutade | 4 | 5 | 5 | 2 | 4 | 5 | 3 | 4 | 5 | 3 | 5 | 5 | 2 | 4 | 5 | 3 | 5 | 5 | 2 | 5 | 5 | 4 | 4 | 5 |
| | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| | Green | 4 | 5 | 5 | 1 | 2 | 3 | 1 | 3 | 4 | 2 | 3 | 5 | 2 | 4 | 4 | 2 | 4 | 5 | 2 | 3 | 5 | 3 | 4 | 5 |

-continued

|  |  |  |  |  |  |  |  |  |  |  |  |  |  |  |  |  |  |  |  |  |  |  |  |  |  |  |  |  |  |  |
|---|---|---|---|---|---|---|---|---|---|---|---|---|---|---|---|---|---|---|---|---|---|---|---|---|---|---|---|---|---|---|
| phytotoxicity | foxtail Corn | 2 | 2 | 3 | 0 | 0 | 0 | 0 | 0 | 0 | 0 | 1 | 1 | 0 | 0 | 1 | 0 | 1 | 1 | 0 | 0 | 1 | 0 | 1 | 1 |
|  | Soybeans | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
|  | Cotton | 0 | 2 | 2 | 0 | 0 | 0 | 0 | 0 | 0 | 0 | 1 | 1 | 0 | 0 | 0 | 0 | 0 | 1 | 0 | 0 | 0 | 0 | 1 | 1 |

| | | Compound No. | | | | | | | | | | | | | | | | | | | | | | |
|---|---|---|---|---|---|---|---|---|---|---|---|---|---|---|---|---|---|---|---|---|---|---|---|---|
| Application | | 9 | | | 10 | | | 11 | | | 12 | | | 13 | | | 14 | | | 15 | | | 16 | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 4 | 5 | 5 | 2 | 4 | 5 | 4 | 4 | 5 | 4 | 5 | 5 | 4 | 4 | 5 | 4 | 5 | 5 | 4 | 4 | 5 | 4 | 4 | 5 |
|  | Pigweed | 2 | 5 | 5 | 1 | 5 | 5 | 5 | 5 | 5 | 2 | 5 | 5 | 5 | 5 | 5 | 5 | 5 | 5 | 5 | 5 | 5 | 5 | 5 | 5 |
|  | Lamb's-quarters | 3 | 5 | 5 | 3 | 4 | 4 | 4 | 5 | 5 | 3 | 5 | 5 | 4 | 5 | 5 | 4 | 5 | 5 | 3 | 4 | 5 | 4 | 5 | 5 |
|  | Inutade | 2 | 4 | 5 | 1 | 4 | 5 | 1 | 3 | 4 | 4 | 5 | 5 | 2 | 4 | 4 | 2 | 3 | 4 | 1 | 2 | 4 | 2 | 3 | 4 |
|  | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|  | Green foxtail | 1 | 4 | 4 | 1 | 2 | 3 | 2 | 3 | 4 | 3 | 4 | 5 | 2 | 3 | 4 | 2 | 3 | 4 | 3 | 4 | 4 | 3 | 4 | 4 |
| phytotoxicity | Corn | 1 | 1 | 2 | 0 | 0 | 1 | 0 | 0 | 0 | 0 | 0 | 0 | 1 | 1 | 1 | 0 | 0 | 1 | 0 | 0 | 0 | 0 | 0 | 0 |
|  | Soybeans | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |
|  | Cotton | 0 | 0 | 1 | 0 | 0 | 1 | 0 | 0 | 0 | 0 | 0 | 0 | 1 | 1 | 0 | 0 | 1 | 0 | 0 | 0 | 0 | 0 | 0 | 0 |

| | | Compound No. | | | | | | | | | | | | | | | | | | | | | | |
|---|---|---|---|---|---|---|---|---|---|---|---|---|---|---|---|---|---|---|---|---|---|---|---|---|
| Application | | 17 | | | 18 | | | 19 | | | 20 | | | 22 | | | 23 | | | 24 | | | 25 | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 5 | 5 | 5 | 4 | 4 | 5 | 3 | 4 | 4 | 4 | 4 | 5 | 5 | 5 | 5 | 5 | 5 | 5 | 5 | 5 | 5 | 5 | 5 | 5 |
|  | Pigweed | 5 | 5 | 5 | 1 | 2 | 4 | 4 | 4 | 5 | 3 | 4 | 5 | 5 | 5 | 5 | 3 | 5 | 5 | 5 | 5 | 4 | 5 | 5 | 5 |
|  | Lamb's-quaters | 5 | 5 | 5 | 3 | 4 | 5 | 4 | 4 | 5 | 3 | 4 | 5 | 5 | 5 | 5 | 5 | 5 | 5 | 5 | 5 | 3 | 4 | 5 | 5 |
|  | Inutade | 4 | 4 | 5 | 1 | 1 | 3 | 1 | 2 | 3 | 1 | 3 | 5 | 4 | 5 | 5 | 4 | 5 | 5 | 5 | 5 | 5 | 3 | 5 | 5 |
|  | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|  | Green foxtail | 4 | 4 | 5 | 3 | 3 | 3 | 2 | 2 | 4 | 1 | 2 | 4 | 4 | 5 | 5 | 3 | 5 | 5 | 4 | 5 | 5 | 2 | 4 | 5 |
| phytotoxicity | Corn | 1 | 2 | 2 | 0 | 1 | 1 | 0 | 1 | 1 | 0 | 1 | 1 | 1 | 1 | 2 | 0 | 1 | 2 | 1 | 1 | 2 | 0 | 0 | 2 |
|  | Soybeans | 0 | 1 | 1 | 0 | 0 | 0 | 0 | 0 | 0 | 0 | 0 | 0 | 0 | 0 | 1 | 0 | 0 | 0 | 0 | 0 | 1 | 0 | 0 | 1 |
|  | Cotton | 1 | 1 | 1 | 0 | 0 | 0 | 0 | 0 | 0 | 0 | 0 | 1 | 1 | 1 | 2 | 0 | 0 | 1 | 0 | 0 | 1 | 0 | 0 | 2 |

| | | Compound No. | | | | | | | | | | | | | | | | | | | | | | |
|---|---|---|---|---|---|---|---|---|---|---|---|---|---|---|---|---|---|---|---|---|---|---|---|---|
| Application | | 26 | | | 27 | | | 28 | | | 29 | | | 30 | | | 31 | | | 33 | | | 34 | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 5 | 5 | 5 | 5 | 5 | 5 | 5 | 5 | 5 | 4 | 5 | 5 | 5 | 5 | 5 | 4 | 4 | 5 | 4 | 5 | 5 | 4 | 4 | 5 |
|  | Pigweed | 5 | 5 | 5 | 5 | 5 | 5 | 5 | 5 | 5 | 4 | 5 | 5 | 5 | 5 | 5 | 4 | 4 | 5 | 5 | 5 | 5 | 5 | 5 | 5 |
|  | Lamb's-quarters | 4 | 5 | 5 | 4 | 4 | 5 | 4 | 5 | 5 | 4 | 5 | 5 | 5 | 5 | 5 | 4 | 4 | 5 | 5 | 5 | 5 | 5 | 5 | 5 |
|  | Inutade | 5 | 5 | 5 | 4 | 5 | 5 | 5 | 5 | 5 | 4 | 4 | 5 | 4 | 4 | 5 | 1 | 2 | 4 | 5 | 5 | 5 | 5 | 5 | 5 |
|  | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|  | Green foxtail | 4 | 5 | 5 | 4 | 5 | 5 | 4 | 5 | 5 | 2 | 4 | 5 | 2 | 4 | 4 | 1 | 3 | 4 | 3 | 5 | 5 | 2 | 4 | 5 |
| phytotoxicity | Corn | 0 | 1 | 1 | 0 | 1 | 2 | 1 | 1 | 2 | 0 | 1 | 1 | 0 | 0 | 0 | 0 | 0 | 1 | 1 | 1 | 2 | 0 | 1 | 2 |
|  | Soybeans | 0 | 0 | 1 | 0 | 0 | 1 | 0 | 0 | 1 | 0 | 0 | 0 | 0 | 0 | 0 | 0 | 0 | 0 | 0 | 0 | 0 | 0 | 0 | 0 |
|  | Cotton | 0 | 0 | 2 | 0 | 0 | 1 | 0 | 0 | 1 | 0 | 0 | 1 | 0 | 0 | 0 | 0 | 0 | 0 | 0 | 0 | 1 | 0 | 0 | 1 |

| | | Compound No. | | | | | | | | | | | | | | | | | | | | | | |
|---|---|---|---|---|---|---|---|---|---|---|---|---|---|---|---|---|---|---|---|---|---|---|---|---|
| Application | | 35 | | | 36 | | | 37 | | | 38 | | | 39 | | | 40 | | | 41 | | | 42 | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 5 | 5 | 5 | 4 | 5 | 5 | 4 | 5 | 5 | 3 | 4 | 5 | 4 | 5 | 5 | 4 | 4 | 5 | 3 | 4 | 4 | 3 | 4 | 5 |
|  | Pigweed | 4 | 5 | 5 | 5 | 5 | 5 | 5 | 5 | 5 | 4 | 5 | 5 | 5 | 5 | 5 | 5 | 5 | 5 | 4 | 4 | 5 | 4 | 5 | 5 |
|  | Lamb's quarters | 4 | 5 | 5 | 4 | 4 | 5 | 4 | 5 | 5 | 2 | 4 | 5 | 4 | 5 | 5 | 4 | 5 | 5 | 3 | 4 | 4 | 4 | 5 | 5 |
|  | Inutade | 4 | 5 | 5 | 2 | 4 | 5 | 3 | 5 | 5 | 1 | 2 | 3 | 2 | 4 | 4 | 2 | 5 | 5 | 1 | 2 | 4 | 3 | 4 | 4 |
|  | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|  | Green foxtail | 4 | 5 | 5 | 3 | 4 | 5 | 4 | 5 | 5 | 2 | 3 | 4 | 3 | 4 | 5 | 1 | 3 | 5 | 1 | 2 | 4 | 3 | 4 | 4 |
| phytotoxicity | Corn | 0 | 0 | 1 | 0 | 0 | 1 | 0 | 0 | 1 | 0 | 0 | 0 | 0 | 0 | 0 | 0 | 0 | 1 | 0 | 1 | 1 | 0 | 1 | 1 |
|  | Soybeans | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
|  | Cotton | 0 | 0 | 0 | 0 | 0 | 0 | 0 | 0 | 1 | 0 | 0 | 0 | 0 | 0 | 0 | 0 | 0 | 1 | 0 | 0 | 0 | 0 | 0 | 0 |

| | | Compound No. | | | | | | | | | | | | | | | | | | | | | | |
|---|---|---|---|---|---|---|---|---|---|---|---|---|---|---|---|---|---|---|---|---|---|---|---|---|
| Application | | 43 | | | 44 | | | 45 | | | 46 | | | 47 | | | 48 | | | 49 | | | 50 | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 5 | 5 | 5 | 4 | 5 | 5 | 5 | 5 | 5 | 4 | 5 | 5 | 5 | 5 | 5 | 4 | 4 | 4 | 4 | 4 | 5 | 4 | 4 | 5 |
|  | Pigweed | 5 | 5 | 5 | 5 | 5 | 5 | 5 | 5 | 5 | 3 | 4 | 5 | 3 | 5 | 5 | 3 | 5 | 4 | 4 | 5 | 5 | 3 | 4 | 4 |
|  | Lamb's-quarters | 5 | 5 | 5 | 5 | 5 | 5 | 5 | 5 | 5 | 5 | 5 | 5 | 5 | 5 | 5 | 3 | 4 | 4 | 3 | 4 | 5 | 4 | 5 | 5 |
|  | Inutade | 4 | 5 | 5 | 4 | 4 | 5 | 3 | 4 | 5 | 3 | 4 | 5 | 4 | 5 | 5 | 1 | 3 | 4 | 2 | 3 | 4 | 1 | 3 | 4 |
|  | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|  | Green foxtail | 4 | 5 | 5 | 4 | 4 | 5 | 4 | 4 | 5 | 3 | 4 | 5 | 4 | 5 | 5 | 1 | 3 | 3 | 2 | 3 | 4 | 1 | 3 | 4 |

-continued

| phytotoxicity | Corn | 1 | 1 | 2 | 1 | 1 | 2 | 2 | 2 | 2 | 0 | 1 | 1 | 0 | 0 | 1 | 0 | 0 | 0 | 0 | 0 | 1 | 0 | 0 | 0 |
|---|---|---|---|---|---|---|---|---|---|---|---|---|---|---|---|---|---|---|---|---|---|---|---|---|---|
| | Soybeans | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| | Cotton | 0 | 1 | 2 | 0 | 0 | 0 | 0 | 0 | 1 | 0 | 0 | 0 | 0 | 0 | 0 | 0 | 0 | 0 | 0 | 0 | 0 | 0 | 0 | 0 |

| | | | Compound No. | | | | | | | | | | | | | | | | | | | | | | |
|---|---|---|---|---|---|---|---|---|---|---|---|---|---|---|---|---|---|---|---|---|---|---|---|---|---|
| Application | | 51 | | | 52 | | | 53 | | | 54 | | | 55 | | | 56 | | | 57 | | | 58 | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 4 | 4 | 4 | 4 | 5 | 5 | 5 | 5 | 5 | 4 | 5 | 5 | 4 | 5 | 5 | 5 | 5 | 5 | 5 | 5 | 5 | 4 | 5 | 5 |
| | Pigweed | 4 | 5 | 5 | 5 | 5 | 5 | 5 | 5 | 5 | 5 | 5 | 5 | 1 | 4 | 5 | 5 | 5 | 5 | 5 | 5 | 5 | 5 | 5 | 5 |
| | Lamb's-quarters | 5 | 5 | 5 | 4 | 5 | 5 | 5 | 5 | 5 | 5 | 5 | 5 | 4 | 4 | 5 | 5 | 5 | 4 | 4 | 5 | 4 | 4 | 5 | 5 |
| | Inutade | 1 | 3 | 4 | 4 | 5 | 5 | 5 | 5 | 5 | 4 | 5 | 5 | 4 | 5 | 5 | 4 | 5 | 5 | 5 | 5 | 5 | 2 | 4 | 5 |
| | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| | Green foxtail | 1 | 3 | 3 | 2 | 4 | 5 | 3 | 4 | 5 | 3 | 4 | 4 | 2 | 3 | 5 | 3 | 4 | 5 | 4 | 5 | 5 | 4 | 4 | 5 |
| phytotoxicity | Corn | 0 | 0 | 0 | 0 | 1 | 1 | 1 | 1 | 1 | 1 | 1 | 1 | 0 | 0 | 0 | 0 | 1 | 2 | 1 | 2 | 2 | 0 | 1 | 2 |
| | Soybeans | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 1 |
| | Cotton | 0 | 0 | 0 | 0 | 1 | 2 | 1 | 1 | 2 | 0 | 2 | 2 | 0 | 0 | 0 | 0 | 0 | 0 | 0 | 0 | 0 | 0 | 0 | 1 |

| | | | Compound No. | | | | | | | | | | | | | | | | | | | | | | |
|---|---|---|---|---|---|---|---|---|---|---|---|---|---|---|---|---|---|---|---|---|---|---|---|---|---|
| Application | | 59 | | | 60 | | | 61 | | | 62 | | | 63 | | | 64 | | | 65 | | | 66 | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 5 | 5 | 5 | 5 | 5 | 5 | 4 | 5 | 5 | 4 | 5 | 5 | 5 | 5 | 5 | 5 | 5 | 5 | 5 | 4 | 5 | 5 | 5 | 5 |
| | Pigweed | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| | Lamb's-quarters | 5 | 5 | 5 | 5 | 5 | 5 | 5 | 5 | 5 | 5 | 5 | 5 | 5 | 5 | 4 | 5 | 5 | 4 | 5 | 5 | 5 | 5 | 5 | 5 |
| | Inutade | 5 | 5 | 5 | 5 | 5 | 5 | 4 | 5 | 5 | 4 | 5 | 5 | 5 | 5 | 5 | 5 | 5 | 5 | 3 | 4 | 5 | 2 | 4 | 4 |
| | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| | Green foxtail | 4 | 5 | 5 | 3 | 5 | 5 | 3 | 4 | 5 | 2 | 4 | 5 | 4 | 5 | 5 | 5 | 5 | 5 | 4 | 4 | 5 | 3 | 4 | 5 |
| phytotoxicity | Corn | 1 | 2 | 2 | 1 | 1 | 2 | 0 | 0 | 1 | 0 | 1 | 1 | 1 | 1 | 2 | 1 | 1 | 2 | 0 | 1 | 2 | 0 | 1 | 2 |
| | Soybeans | 0 | 0 | 1 | 0 | 1 | 1 | 0 | 0 | 1 | 0 | 0 | 0 | 0 | 0 | 0 | 0 | 1 | 0 | 0 | 0 | 0 | 0 | 0 | 0 |
| | Cotton | 0 | 0 | 1 | 1 | 1 | 2 | 0 | 0 | 1 | 0 | 1 | 2 | 0 | 0 | 0 | 0 | 1 | 0 | 0 | 0 | 1 | 0 | 1 | 1 |

| | | | Compound No. | | | | | | | | | | | | | | | | | | | | | | |
|---|---|---|---|---|---|---|---|---|---|---|---|---|---|---|---|---|---|---|---|---|---|---|---|---|---|
| Application | | 67 | | | 70 | | | 71 | | | 72 | | | 73 | | | 74 | | | 75 | | | 76 | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 4 | 4 | 4 | 4 | 5 | 5 | 5 | 5 | 4 | 5 | 5 | 4 | 5 | 5 | 5 | 5 | 5 | 4 | 5 | 5 | 5 | 5 | 5 | 5 |
| | Pigweed | 3 | 4 | 5 | 2 | 5 | 5 | 4 | 5 | 5 | 5 | 5 | 4 | 4 | 4 | 5 | 5 | 5 | 5 | 5 | 5 | 5 | 5 | 5 | 5 |
| | Lamb's-quarters | 3 | 4 | 5 | 3 | 5 | 5 | 4 | 4 | 5 | 4 | 4 | 3 | 4 | 5 | 5 | 5 | 5 | 4 | 4 | 4 | 5 | 5 | 5 | 5 |
| | Inutade | 2 | 3 | 4 | 2 | 4 | 4 | 2 | 3 | 5 | 1 | 3 | 4 | 2 | 4 | 4 | 3 | 4 | 5 | 2 | 4 | 4 | 3 | 4 | 5 |
| | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| | Green foxtail | 1 | 3 | 4 | 2 | 4 | 5 | 2 | 2 | 4 | 3 | 3 | 4 | 2 | 3 | 4 | 3 | 4 | 5 | 2 | 3 | 4 | 4 | 4 | 5 |
| phytotoxicity | Corn | 0 | 0 | 1 | 0 | 1 | 1 | 0 | 0 | 1 | 0 | 1 | 1 | 0 | 0 | 0 | 1 | 1 | 1 | 0 | 0 | 0 | 0 | 1 | 1 |
| | Soybeans | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 1 |

| | | | | | | | | Compound No. | | | | | | | | | | | Compound A | | |
|---|---|---|---|---|---|---|---|---|---|---|---|---|---|---|---|---|---|---|---|---|---|---|
| Application | | 77 | | | 78 | | | 79 | | | 80 | | | 82 | | | 83 | | | | | |
| rate g/a | | 5 | 10 | 20 | 5 | 10 | 20 | 5 | 10 | 20 | 5 | 10 | 20 | 5 | 10 | 20 | 5 | 10 | 20 | 5 | 10 | 20 |
| Effect | Crab grass | 5 | 5 | 5 | 4 | 5 | 5 | 4 | 5 | 5 | 4 | 5 | 5 | 2 | 4 | 5 | 4 | 4 | 5 | 1 | 3 | 3 |
| | Pigweed | 5 | 5 | 5 | 5 | 5 | 5 | 5 | 5 | 5 | 5 | 5 | 5 | 2 | 3 | 5 | 5 | 5 | 5 | 2 | 4 | 4 |
| | Lamb's-quarters | 5 | 5 | 5 | 5 | 5 | 5 | 5 | 5 | 4 | 5 | 5 | 2 | 4 | 4 | 5 | 5 | 5 | 1 | 3 | 3 | | |
| | Inutade | 4 | 4 | 5 | 3 | 4 | 5 | 3 | 4 | 5 | 2 | 4 | 4 | 1 | 2 | 4 | 3 | 4 | 5 | 1 | 1 | 1 |
| | Common purslane | 5 | 5 | 5 | 5 | 5 | 5 | 5 | 5 | 5 | 5 | 5 | 5 | 5 | 5 | 5 | 5 | 5 | 5 | 5 | 5 | 5 |
| | Green foxtail | 4 | 4 | 5 | 2 | 4 | 5 | 3 | 4 | 4 | 3 | 4 | 5 | 1 | 2 | 3 | 2 | 4 | 5 | 1 | 1 | 1 |
| phytotoxicity | Corn | 1 | 1 | 1 | 0 | 1 | 1 | 0 | 0 | 1 | 1 | 1 | 1 | 0 | 0 | 0 | 0 | 1 | 1 | 0 | 0 | 0 |
| | Soybeans | 0 | 0 | 0 | 0 | 0 | 0 | 0 | 0 | 0 | 0 | 0 | 0 | 0 | 0 | 0 | 0 | 0 | 0 | 0 | 0 | 0 |
| | Cotton | 0 | 0 | 1 | 0 | 0 | 1 | 0 | 0 | 0 | 0 | 0 | 1 | 0 | 0 | 0 | 0 | 1 | 0 | 0 | 0 | 0 |

I claim:

1. A compound represented by the formula

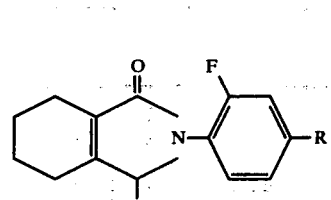

wherein R is a halogen; Q is (1) hydrogen, (2) a straight-chain or branched (C$_{1-11}$) alkyl group which may be substituted by a hydroxyl group, a cyano group, a (C$_{2-4}$) alkanoyl group, a benzoyl group or a (C$_{1-4}$) alkoxycarbonyl group, (3) a benzyl group, (4) a (C$_{2-6}$) alkenyl group, (5) a phenyl group, (6) R$_1$S, (7) R$_2$CO, or (8)

wherein R$^1$ is selected from a straight-chain or branched (C$_{1-11}$) alkyl group, a phenyl group which may be substituted by a halogen, or

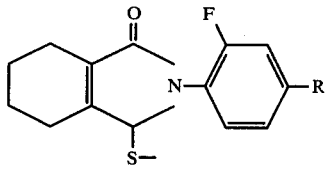

wherein
  R is as defined above;
  R$_2$ is selected from a straight-chain or branched (C$_{1-11}$) alkyl group which may be substituted by a (C$_{1-4}$) alkoxy group, or a phenyl group which may be substituted by a halogen or a (C$_{1-4}$) alkyl group;
  R$_3$ is selected from a straight-chain or branched (C$_{1-11}$) alkyl group, a (C$_{2-6}$) alkenyl group, a cyclohexyl group, a benzyl group, or a phenyl group which may be substituted by a halogen or a (C$_{1-4}$) alkyl group;
  X is selected from oxygen or an imino group which may be substituted by a (C$_{1-4}$) alkyl group; and
  Y and Z are each selected from oxygen or sulfur.

2. A compound as claimed in claim 1, wherein R is chlorine.

3. A compound as claimed in claims 1 or 2, wherein Q is hydrogen.

4. A compound as claimed in claims 1 or 2, wherein Q is R$_1$S.

5. A compound as claimed in claim 4, wherein R$_1$ is a lower alkyl, phenyl which may be substituted by a chlorine atom, or

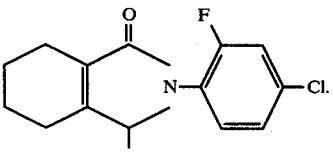

6. A compound as claimed in claim 5, wherein the lower alkyl is methyl.

7. A compound as claimed in claim 5, wherein R$_1$ is

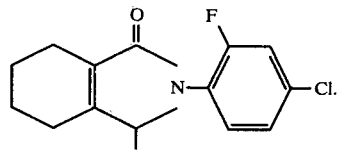

8. A compound as claimed in claims 1 or 2, wherein Q is R$_2$CO.

9. A compound as claimed in claim 8, wherein R$_2$ is a straight-chain lower alkyl.

10. A compound as claimed in claim 9, wherein the straight-chain lower alkyl is n-propyl.

11. A compound as claimed in claims 1 or 2, wherein Q is

12. A compound as claimed in claim 11, wherein X is

Y is oxygen or sulphur, and R$_3$ is a lower alkyl, cyclohexyl, allyl, benzyl, phenyl which may be substituted by a chlorine atom or a methyl group.

13. A compound as claimed in claim 12, wherein the lower alkyl is methyl.

14. The compound of claim 1 wherein Q is hydrogen, a lower alkylthio, a lower alkanoyl, or a lower alkyl carbamoyl group.

15. A herbicidal composition comprising a herbicidally effective amount of the compound of claim 1, in combination with an inert carrier.

16. The herbicidal composition of claim 15, wherein said carrier is a solid or a liquid.

17. The herbicidal composition of claim 16, wherein said liquid carrier is selected from water, alcohol, ketone, ether, aliphatic hydrocarbon, aromatic hydrocarbon, halogenated hydrocarbon, acid amide, ester, nitrile or a mixture thereof.

18. The herbicidal composition of claim 16, wherein said solid carrier is selected from vegetable powder, mineral powder, alumina, sulfur powder, activated carbon or a mixture thereof.

19. The herbicidal composition of claim 15, wherein said composition is in the form of an emulsifiable concentrate or wettable powder and said herbicidally effective amount is 10 to 90 weight percent.

20. The herbicidal composition of claim 15, wherein said composition is in the form of an oil solution or dust and said herbicidally effective amount is 0.1 to 10 weight percent.

21. The herbicidal composition of claim 15, wherein said composition is in the form of granules and said herbicidally effective amount is 1 to 20 weight percent.

* * * * *